(12) United States Patent
Huang et al.

(10) Patent No.: US 7,976,743 B2
(45) Date of Patent: Jul. 12, 2011

(54) GAS-CONTAINING LIPOSOMES

(75) Inventors: Shaoling Huang, Sugar Land, TX (US); Patrick Kee, Houston, TX (US); Robert C. MacDonald, El Cerrito, CA (US); David McPherson, Houston, TX (US)

(73) Assignees: Northwestern University, Evanston, IL (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/873,256

(22) Filed: Oct. 16, 2007

(65) Prior Publication Data
US 2008/0175893 A1    Jul. 24, 2008

Related U.S. Application Data

(60) Provisional application No. 60/852,134, filed on Oct. 16, 2006.

(51) Int. Cl.
*A61K 9/127* (2006.01)
*A61K 51/00* (2006.01)
*C12N 15/88* (2006.01)

(52) U.S. Cl. ......... 264/4.1; 424/1.21; 435/458; 977/907

(58) Field of Classification Search .................. 264/4.1; 424/1.21; 435/458; 977/907
See application file for complete search history.

(56) References Cited

U.S. PATENT DOCUMENTS 4,900,540 A * 2/1990 Ryan et al. ............... 424/9.51
7,033,574 B1 * 4/2006 Schneider et al. .......... 424/9.52

FOREIGN PATENT DOCUMENTS

EP          0707846 A2 *  4/1996
WO       WO 85/04326    * 10/1985

OTHER PUBLICATIONS

Van Winden et al., 1997, Pharmaceutical Research, vol. 14, No. 9, p. 1151-1160.*

Li et al., 2004, Journal of Pharmaceutical Sciences, vol. 93, No. 6, p. 1403-1414.*
Levi et al., 2003, Diabetes, Obesity and Metabolism, vol. 5, p. 45-50.*
Van Winden et al., "Effect of Freezing Rate on the Stability of Liposomes During Freeze-Drying and Rehydration," 1997, Pharmaceutical Research, vol. 14, No. 9, p. 1151-1160.
Li et al., 2004, "A Novel Method for the Preparation of Liposomes: Freeze Drying of Monophase Solutions," Journal of Pharmaceutical Sciences, vol. 93, No. 6, p. 1403-1414.
Miller and Megson", Recent developments in nitric oxide donor drugs," British J. Pharm. 2007; 151: 305-321.
Shohet et al., "Echocardiographic Destruction of Albumin Microbubbles Directs Gene Delivery to the Myocardium," Circulation 2000; 101(22): 2554-6.
Smith et al., "Destruction Thresholds of Echogenic Liposomes with Clinical Diagnostic Ultrasound," Ultrasound Med Biol. May 2007; 33(5):797-809.
Huang and MacDonald," Acoustically active liposomes for drug encapsulation and ultrasound-triggered release," Biochim Biophys Acta. Oct. 11, 2004;1665(1-2):134-41.
Porter et al., "Interaction of Diagnostic Ultrasound with Synthetic Oligonucleotide-Labeled Perfluorocarbon-Exposed Sonicated Dextrose Albumin Microbubbles," J Ultrasound Med 1996;15(8):577-84.
Huang et al., "Acoustically-Active Liposomes of Novel Cationic-Anionic Composition in Conjuction with Ultrasound for Gene Delivery into Vascular Smooth Muscle Cells," Mol Ther. 2003;7(5)422 Part 2.
Huang et al., "Physical Correlates of the Ultrasonic Reflectivity of Lipid Dispersions Suitable as Diagnostic Contrast Agents," Ultrasound Med Biol. 2002;28(3):339-48.
Nakatsubo, et al. "Direct evidence of nitric oxide production from bovine aortic endothelial cells using new fluorescence indicators: diaminofluoresceins," FEBS Letters 1998;427(2):263-6.

* cited by examiner

*Primary Examiner* — Shin-Lin Chen
(74) *Attorney, Agent, or Firm* — Casimir Jones, S.C.

(57) ABSTRACT

The present invention provides gas-containing liposomes. In particular, the present invention provide methods of generating gas-containing liposomes where the gas is introduced under pressure, as well as gas-containing liposomes which contain a large volume of gas (e.g., 10 ul of gas per 5 mg of gas-containing liposomes). In certain embodiments, the gas-containing liposomes contain nitric oxide gas. In some embodiments, such nitric oxide containing liposomes are used to treat a medical condition that is treatable by nitric oxide gas (e.g., intimal hyperplasia).

7 Claims, 11 Drawing Sheets

A.

B.

Cell viability at 4 hours after nitric oxide loaded liposome delivery. viability was measured by calcein AM.

EFFECT of NO containing liposomes on inhibition of intimal hyperplasia on balloon-injured rabbits. Mean +/- SD, n=3

GAS-CONTAINING LIPOSOMES

The present application claims priority to U.S. Provisional Application Ser. No. 60/852,134, filed Oct. 16, 2006, which is herein incorporated by reference in its entirety.

This invention was made with government support under Grant No. HL074002-01 awarded by the National Institutes of Health. The government has certain rights in the invention.

FIELD OF THE INVENTION

The present invention relates to gas-containing liposomes. In particular, the present invention relates, in some embodiments, to methods generating gas-containing liposomes using a unique sequence of steps wherein the lipid suspension is equilibrated with the gas of choice under elevated pressure, frozen, returned to ambient pressure and thawed. This procedure produces liposomes that contain a large volume of gas (e.g. 5 ul or more per mg lipid). In certain embodiments, the gas-containing liposomes contain nitric oxide gas. In some embodiments, such nitric oxide containing liposomes are used to treat a medical condition that is treatable by nitric oxide gas (e.g., intimal hyperplasia).

BACKGROUND OF THE INVENTION

The bioactive effect of Nitric oxide (Chemical formula NO) was found in 1992. Soon after, its effect on the human body has been extensively investigated. The most studied actions of NO are in the cardiovascular system, where it is produced by vascular endothelial and plays a crucial role in vascular tone and structure regulation. This vasodilator tone plays an important role in regulation of blood flow in healthy humans. Except its vascular dilation effect, NO has exerts an anti-atherogenic effects due to its anti-inflammatory influence, limiting the development of the complex plaque, inhibiting platelets adhesion and aggregation, preventing smooth muscle cells proliferation and migration. Given the multiple actions of NO on cardiovascular medicine, delivery of exogenous NO is an attractive therapeutic option for the treatment of atherosclerosis. NO molecule is a free radical, which has high reactivity with the oxygen in air to form nitrogen dioxide. Such chemical character of NO has led to the synthesis of a variety of NO donors. NO donors are molecular carriers of NO to stabilize the radical until its release in circulation. Each NO donor has different rates of NO release and is tailored to different drugs to suit the disease target. However, the long-term use of current NO donor is limited by development of tolerance and toxicity issues. This gives rise to a clinical need for novel alternative delivery methods (see, Miller and Megson, Recent developments in nitric oxide donor drugs. British J. Pharm. 2007; 151: 305-321, herein incorporated by reference).

NO gas itself has been directly used in pulmonary hypertension. In such specific cases, the NO is delivered by inhalation. Recently, such delivery method has been used in the treatment of restenosis. However, the systemic NO delivery might be limited by unwanted side effects outside the target tissue due to its enormous variety of effects of NO in different tissues. As such, what is needed are methods, compositions, and systems for delivery of NO to treat diseases, such as atheroclothesis, as well as methods for in vivo imaging and triggering methods such that NO can be delivered at the desired site.

SUMMARY OF THE INVENTION

The present invention provides gas-containing liposomes. In particular, the present invention provides, in some embodiments, to methods generating gas-containing liposomes using a unique sequence of steps wherein the lipid suspension is equilibrated with the gas of choice under elevated pressure, frozen, returned to ambient pressure and thawed. This procedure produces liposomes that contain a large volume of gas (e.g. 5 ul or more per mg lipid). In certain embodiments, the gas-containing liposomes contain nitric oxide gas. In some embodiments, such nitric oxide containing liposomes are used to treat a medical condition that is treatable by nitric oxide gas (e.g., intimal hyperplasia).

In some embodiments, the present invention provides a method of making a gas-containing liposome, comprising: freezing under pressure, liposomes with gas, to generate a gas-liposome dispersion; and thawing said gas-liposome dispersion to generate a plurality of gas-containing liposomes. For example, in some embodiments, the present invention provides methods of making a gas-containing liposome, comprising one or more of the following steps: a) generating a thin film of lipids using an organic solvent; b) removing the organic solvent to generate a dried lipid film; c) hydrating the dried lipid film with an hydrating solution to generate liposomes; d) sonicating the liposomes; e) combining the liposomes with gas under pressure to generate a gas-liposome dispersion; f) freezing the gas-liposome dispersion; g) thawing the gas-liposome dispersion to generate a plurality of gas-containing liposomes. In certain embodiments, the method comprises equilibrating a lipid suspension with a gas under elevated pressure, freezing the lipid suspension, returning the lipid suspension to ambient or near ambient pressure and thawing the suspension.

In preferred embodiments, the pressure is released from the gas-liposome dispersion prior to thawing. In some embodiments, the pressure is released from the gas-liposome dispersion during the thawing. In some embodiments, the pressure is released only after the thawing step. In some embodiments, each of the gas-containing liposomes contain between 4-8 percent of the gas by volume. In particular embodiments, the gas-containing liposomes comprise at least 10 ul of gas per 5 mg of the gas-containing liposomes (e.g., between 10-25 or between 15-30 ul, or between 20-50 ul, of gas per 5 mg of gas containing liposomes). In further embodiments, the gas-containing liposomes comprise at least 20 ul, or at least 30 ul, or at least 40 ul, or at least 45 ul, or at least 50 ul, of gas per 5 mg of the gas-containing liposomes. In other embodiments, the gas-containing liposomes comprise at least 30 ul of gas per 5 mg of the gas-containing liposomes.

The present invention is not limited by the type of gas that is employed. Any suitable gas is contemplated. In certain embodiments, the gas is selected from air, any component of air (e.g., nitrogen), nitric oxide, a perflourocarbon, argon, carbon monoxide, hyperpolarized xenon (e.g, which could be employed where the liposomes are exposed to a laser beam), or other bioactive gases. In other embodiments, the gas is selected from xenon, hyperpolarized xenon, helium, argon, radon, or carbon monoxide. In particular embodiments, the gas is selected from hyperpolarized helium, sevoflurane, desflurane, isoflurane, halothane, ozone, or similar gasses.

The present invention is not limited by the type of materials used to make the liposomes. Reagents used to make liposomes are well known in the art. In particular embodiments, the gas-containing liposomes comprises phospholipids and cholesterol. In certain embodiments, the liposomes are composed of phospholipids or their derivates and, optionally, cholesterol. In other embodiments, for specific applications, it may be desirable to include smaller amounts of lipid bilayer-compatible hydrophobic molecules. Or, alternatively, for specific applications, it may be desirable modify the properties of the lipid bilayer by inclusion of smaller amounts of hydrophobic molecules.

In other embodiments, the gas-containing liposomes further comprise a second gas, wherein the second gas is configured to regulate the release rate of the nitric oxide from the liposome. In certain embodiments, the present invention provides compositions comprising a plurality of gas-containing liposomes, wherein the gas-containing liposomes comprise at least 15 ul of gas per 5 mg of the gas-containing liposomes (e.g., between 15-25 ul of gas per mg of gas-containing liposomes). In some embodiments, the gas-containing liposomes comprise at least 15 ul of the gas per 5 mg of the liposomes. In further embodiments, the gas-containing liposomes comprise at least 30 ul of the gas per 5 mg of the liposomes.

In particular embodiments, the gas-containing liposomes further comprise an antibody or other targeting moiety configured for targeting the gas-containing liposomes to a specific target in vivo. In other embodiments, the gas-containing liposomes further comprise a second gas, wherein the second gas is configured to regulate the release rate of the gas from the liposome.

In some embodiments, the present invention provides compositions comprising a liposome, wherein the liposome comprise gas (e.g., nitric oxide gas or carbon dioxide gas). In certain embodiments, the liposome is echogenic (e.g., can be visualized by ultrasound). In further embodiments, the liposome further comprises an antibody (or other targeting moiety) configured for targeting the liposome to a specific target in vivo. In particular embodiments, the liposome comprises phospholipids and cholesterol. In other embodiments, the liposome further comprises a second gas, wherein the second gas is configured to regulate the release rate of the nitric oxide from the liposome (e.g., an inert gas, or a non-reactive gas such as nitrogen or argon). In some embodiments, the second gas comprises argon.

In particular embodiments, the present invention provides compositions a plurality of liposomes, wherein the liposomes comprise nitric oxide gas. In certain embodiments, the liposomes the liposomes comprise at least 5 ul, at least 10 ul, at least 15 ul, at least 20 ul, at least 25 ul, or at least 30 ul, or at least 40 ul, or at least 50 ul, of the nitric oxide gas per 5 mg of the liposomes. In other embodiments, the liposomes comprise nitric oxide gas between 5 ul and 30 ul of nitric oxide gas per 5 mg of liposomes. In additional embodiments, the liposomes are echogenic. In particular embodiments, the liposomes further comprise an antibody configured for targeting the liposomes to a specific target in vivo. In further embodiments, the liposomes comprises phospholipids and cholesterol. In other embodiments, the liposomes further comprise a second gas, wherein the second gas is configured to regulate the release rate of the nitric oxide from the liposome.

In some embodiments, the present invention provides methods for treating a medical condition comprising: administering a composition to a patient, wherein the composition comprises a plurality of liposomes, wherein the liposomes comprise gas; wherein the patient has a medical condition that is at least partially treatable by gas; and wherein the administering is under conditions such that the gas is released in the patient. In certain embodiments, the methods further comprise visualizing the location of the liposomes in the patient via ultrasound or other visualization method. In other embodiments, the methods further comprise causing the nitric oxide gas to be released in the patient by subjecting the patient to a triggering therapy (e.g., ultrasound or light treatment). In certain embodiments, ultrasound of the appropriate intensity and frequency is applied to change the rate of release of the gas (see, e.g., Smith et al., Ultrasound Med Biol. 2007 May; 33(5):797-809; and Huang and MacDonald, Biochim Biophys Acta. 2004 Oct. 11;1665(1-2):134-41; both of which are herein incorporated by reference.

In further embodiments, the medical condition is a cardiovascular condition. In particular embodiments, the cardiovascular condition comprises intimal hyperplasia. In some embodiments, the gas (e.g, nitric oxide) is taken up by cells of the patient. In further embodiments, the cells are smooth muscle cells.

In particular embodiments, the present invention provides methods of imaging a patient comprising: a) administering a composition to a patient, wherein the composition comprises a plurality of liposomes, wherein the liposomes comprise gas; and b) visualizing the location of the liposomes in the patient via ultrasound.

In some embodiments, the present invention provides compositions comprising a liposome, wherein the liposome comprises gas and a therapeutic drug useful in the treatment of atheroclothesis, for example rosiglitazone.

In other embodiments, the present invention provides methods of treating a medical condition comprising: administering a composition to a patient, wherein the composition comprises a plurality of liposomes, wherein the liposomes comprise gas and rosiglitazone; and wherein the patient has a medical condition that is at least partially treatable by rosiglitazone. In certain embodiments, the medical condition comprises atheroclothesis.

DESCRIPTION OF THE FIGURES

FIG. 7A shows the stopcock closed and attached to a 250-μL syringe without a plunger, but containing a small volume of water. FIG. 7B shows the plunger of the syringe withdrawn. FIG. 7C shows the plunger then released. FIG. 7D shows the plunger of the large syringe depressed after the stopcock was opened.

FIG. 8B shows a total of 50 µl of NO can be encapsulated in 5 mg of liposomes by the pressured frozen method.

DESCRIPTION OF THE INVENTION

Figure 1:
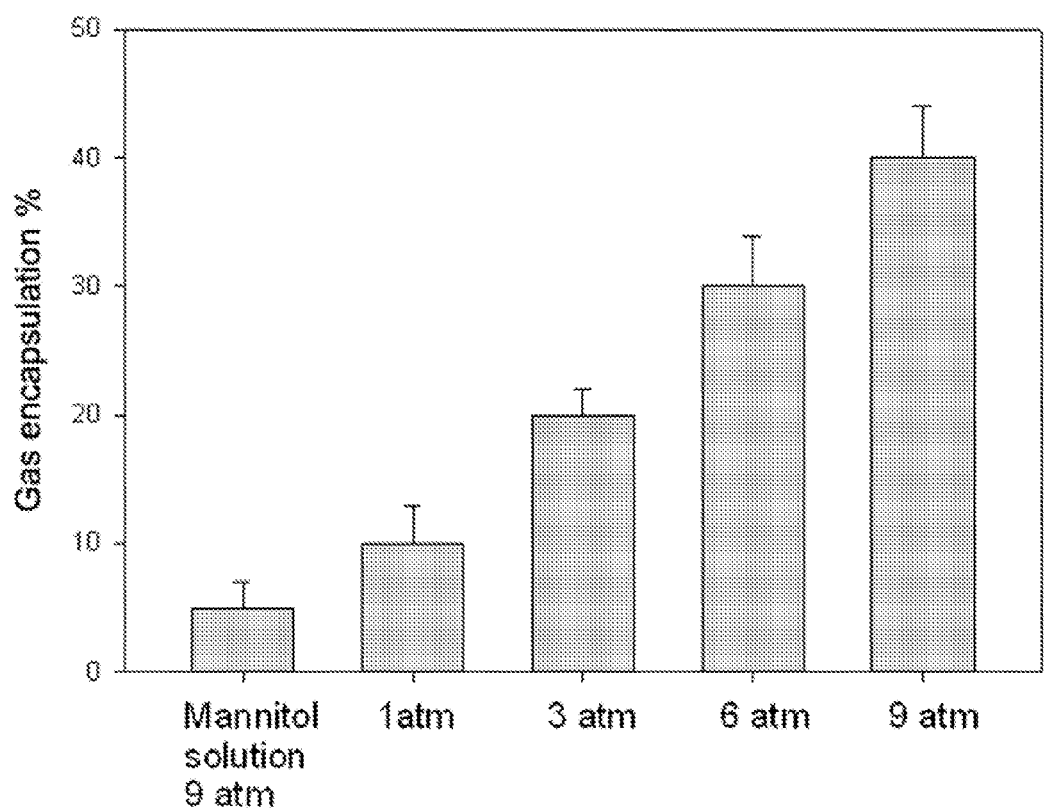
FIG. 1 shows results from Example 1 where gas encapsulation was tested as a function of applied pressure.

The present invention provides gas-containing liposomes. In particular, the present invention provide methods of generating gas-containing liposomes where the gas is introduced under pressure, as well as gas-containing liposomes which contain a large volume of gas (e.g., 10 ul of gas per 5 mg of gas-containing liposomes). In certain embodiments, the gas-containing liposomes contain nitric oxide gas. In some embodiments, such nitric oxide containing liposomes are used to treat a medical condition that is treatable by nitric oxide gas (e.g., intimal hyperplasia).

I. Gas-Containing Liposomes

The present invention, in certain embodiments, provides methods for the facile production of gas-containing liposomes with simultaneous drug encapsulation. In exemplary embodiments (see Example 1), liposomes of phospholipid and cholesterol were prepared by conventional procedures of hydrating the lipid film, sonicating, freezing and thawing. The lipids generated contain air by including a step after sonication where the lipid is placed under pressure with the gas of interest. After equilibration, the sample is frozen. The pressure is then reduced to atmospheric and the suspension thawed. This procedure leads to entrapment of air in amounts up to about 10% by volume by lipid dispersions at moderate (10 mg/ml) concentrations. The amount of gas encapsulated increases with gas pressure and lipid concentration. As shown in Example 1, utilizing 0.32 M mannitol to provide an aqueous phase with physiological osmolarity, 1, 2, 4 or 6 atm of pressure was applied to 4 mg of lipid. This led to encapsulation of 10, 15, 20, and 30 µl of gas, respectively. While the present invention is not limited to any particular mechanism, the mechanism for gas encapsulation presumably depends upon the fact that air (predominantly nitrogen and oxygen), like most solutes, dissolves poorly in ice and is excluded from the ice that forms during freezing. The excluded air then comes out of solution as air pockets that are stabilized in some form by a lipid coating. The presence of air in these preparations sensitizes them to ultrasound such that up to half of their aqueous contents (which could include a water soluble drug) can be released by short (e.g., 10 second) applications of ultrasound.

The present invention provides methods to introduce gas into liposomes such that they not only reflect ultrasound, but also release their contents when exposed to ultrasound or other triggering procedure. Of practical importance is that the method, which, in certain embodiments, uses elevated-pressure in combination with freezing, is very simple and allows ready encapsulation of solutes along with incorporation of a gas of choice. The method is suitable for the preparation of both an ultrasound contrast agent and an ultrasound-controlled drug delivery system.

Conventional procedures for preparing liposomes do not allow for incorporation of a gas because the solubility of gas in water is low. According to Henry's Law, however, the solubility of a gas in a liquid is directly proportional to the pressure of that gas over the liquid. A solution is regarded as undersaturated, saturated or supersaturated when the pressure of the gas is less than, equal to or larger then the equilibrium saturation value in local temperature. Thus, if the pressure is increased, the gas molecule concentration in solution is increased, and when the pressure is lowered, the excess gas is released as vapor.

The pressure-freeze method of certain embodiments of the present invention is based on this principle. An essential role of freezing is to concentrate both gas and solute molecules so as to favor their encapsulation. Indeed, the basic phenomenon, that during freezing, air is released and often trapped as bubbles in the resultant ice, has been know for many years, and, moreover, that bubble formation in cells contributes significantly to freezing damage in long-term preservation of cells and tissues.

Exemplary steps of the methods of the present invention are provided below, particularly in reference to Example 1. Gas incorporation in liposomes was observed to be proportional to pressure. As noted above, this is to be expected from Henry's Law if gas uptake by the liposomes is proportional to the amount in solution at the first step. While this influences gas entrapment, it is the freezing step that has a large influence on dissolved gas and hence on gas encapsulation. While the present invention is not limited to any mechanism, it is believed that freezing probably serves two purposes, increasing the local concentration of dissolved gas and nucleating formation of small pockets of bulk gas phase. Gases, like other solutes, are more soluble in liquid water than in solid ice. Thus, as the ice crystals grow, dissolved gas is progressively displaced from ice to unfrozen solution, with the result that the dissolved gas becomes increasingly concentrated in the ever-diminishing volume of liquid solution. When the dissolved gas concentration becomes sufficiently high, a gas bubble may nucleate and grow. According to the nucleation theory, bubbles form when the difference between the total dissolved gas pressure and the ambient pressure in the surrounding liquid exceeds the La Place pressure (the pressure created in a bubble due to the contraction of the surface under the influence of the surface tension).

Although it is clear that freezing expels the gas from the aqueous phase, it is unknown where the bubbles so expelled reside within the frozen dispersion. In order for the dispersion to become ultrasound-reflective, there must be pockets of air with surfaces of high acoustic impedance. The gas might come out of solution in contact with the hydrophobic interior of the lipid bilayer, which has a relatively low surface tension against air; however, the effect of trehalose on air incorporation suggests a more complex process is involved. Trehalose, which functions as a cryoprotectant by favoring glass formation rather than crystallization (either of itself or of the water), supported much less echogenicity than did mannitol in Example 1 below. Mannitol is rather distinctive among sugars in readily crystallizing out of solution upon cooling. Previously, that art has presented evidence that freezing a mannitol solution inflicts damage upon liposomes. Consistent with that finding and based on nucleation theory is a suggestion made a number of years ago that the polar-nonpolar interface at the surface of damaged membranes may be the preferred site of nucleation of release of nitrogen bubbles in decompression sickness which affects divers who are rapidly decompressed.

Again, while the present invention is not limited to any particular mechanism, the following is believed to be part of the gas-containing liposome formation process. Although supersaturation of the liquid phase during ice formation should cause incipient air pockets to form, it is unlikely that this is the whole story, for, if it were, the echogencity should not be particularly low when samples are thawed prior to reducing the pressure back to ambient pressure. Under these conditions, the ice melts and the water produced is essentially degassed, so air associated with lipid (in all forms) will diffuse into this water. On the other hand, when the pressure is lowered first and the sample thawed second, the air concentration in the solution that melts initially is high because it contains most of the air that dissolved in the suspension upon pressurization. Because of its high solute (mannitol) content, the ice in the environment of the liposomes will melt first and immediately expose the lipid to ambient (1 atm) pressure. This initially melting phase is not only highly supersaturated with air, but it is also likely, as described in the preceding paragraph, to contain air pockets that will grow when exposed to ambient pressure. Hence, air will come out of solution, expanding the gas nuclei that presumably formed during freezing. The result is the formation of air pockets that are stabilized by a monolayer of lipid.

As shown in Example 1, the procedure for gas encapsulation allows simultaneous encapsulation of calcein into liposomes at an efficiency of about 17%. Since this reveals that a substantial portion of the original aqueous phase has been entrapped within the gas-containing liposomes, this also means that a comparable percentage of a drug dissolved in the aqueous phase would also be captured within the liposomes. It seems likely that the air and calcein are entrapped in the same particles because 95% of the FITC-labeled liposomes floated on the top of the sample after mixing echogenic lipid dispersions with 0.32 M mannitol. Since this concentration of mannitol constitutes the predominant solute on the interior of the liposomes, they would have the same density and would not float unless they contained air. Accordingly, it appears that about 95% of the liposomes contained air.

Co-encapsulation of air and an aqueous solute has advantages in drug delivery as it allows for release of liposomal contents by application of ultrasound. Since acoustically active liposomes also reflect ultrasound, it is possible to not only to localize the release of the drug according to the site of application of ultrasound, but also to image the therapeutic agent while it is being activated for delivery. Moreover, targeting of the liposomes themselves is possible.

In addition to releasing liposomal contents and providing an image of the process, ultrasound can have effects on the tissue that synergize with drug delivery, namely cavitation effects of ultrasound which can facilitate access of the drug to its target. For example, prior methods found site-specific drug delivery can be achieved by destroying drug-filled contrast microbubbles in the target area with high-intensity ultrasound (Porter et al., J Ultrasound Med 1996;15(8):577-84.). In addition, Shohet et al. (Circulation 2000;101(22):2554-6.) found that albumin-coated microbubbles could be used to effectively deliver an adenoviral transgene to rat myocardium via US-mediated microbubble destruction. Prior work has also found enhanced uptake of plasmid DNA in the presence of acoustically active liposomes and with the simultaneous application of ultrasound (Huang et al., MOL THER. 2003; 7 (5): 422 Part 2).

The sensitivity of echogenic liposomes to ultrasound stimulation may be able to be improved further by varying the liposomal composition, the encapsulated gas and/or the ultrasound application parameters. The lipid bilayer is held together by hydrophobic interactions that tend to endow it with self-sealing properties such that the lipid shell of a liposome rapidly reseals following surface alternations. It is therefore probable that changing the rigidity of the lipid membrane will affect its response to ultrasound. The choice of the optimal gas will involve both high volume in the liposomes and low rate of release in the blood stream. The most effective ultrasound pulses would seem to be a small number at the highest intensity that the tissue can sustain.

II. Nitric Oxide Containing Liposomes and Exemplary Uses

Nitric oxide and carbon monoxide (CO) are well-known gases with diverse bioactivities and promoting therapeutic agents. However, because of their high reactivity, they are not stable in solution in vitro and will lose activity by binding with hemoglobin in vivo. Although many NO donors have been developed or are under development, none of them are suitable for nitric oxide gas encapsulation and targeted delivery. The same is true for carbon monoxide except that there are fewer carbon dioxide donors commercially available even though the therapeutic effects of CO have been known found for more than a decade. Liposomes, which can encapsulate gases and be conjugated with antibodies for targeted delivery were developed as part of the present invention as vehicles for NO and CO delivery.

During the development of embodiments of the present invention, phosphatidylcholine and cholesterol, with other lipids of either positive or negative charge, were used to make liposomes by a method involving hydrating the lipid film, sonication, and then freezing and thawing. Nitric oxide or a mixture of nitric oxide with another gas was loaded by infection into the lipid dispersion under 4 atm pressures subsequent to the sonication step. The procedure generates liposomes that contain up to 30 ul of gas in 5 mg lipids. As shown in Example 2, passive release of encapsulated NO lasted for about 8 hours with a fast NO release in the first 30 minutes and slow release rate the rest of the time. The release speed can be adjusted by mixing encapsulated NO with an inert gas (e.g., argon or other gas). In some embodiments, with cationic liposomes, nitric oxide can be delivered into cultured cells, resulting in an increase in the production of intracellular cGMP. In other embodiments, with anionic liposomes, antibody can be conjugated for targeting delivery of the liposome and its encapsulated gas. The potent nitric oxide scavenger, hemoglobin, does not generally affect the activity of NO encapsulated in liposomes.

This invention also finds use for NO reflectivity and thus the location of liposomes can be tracked by ultrasound imaging after in vivo administration. Therapeutic NO or CO delivery are active areas in pharmaceutics. The encapsulation and delivery techniques of the invention are highly efficient. Thus, the present invention provides methods for in vitro investigation of the effects of a variety of gases or in vivo therapeutic use for treatment of human diseases such as cardiovascular disease, cancer or inflammatory disorders.

Several advantages provided by embodiments of the present invention include: 1) protection of NO and CO from inactivation; 2) release following an initial rapid release is then constant for more than 8 hours; 3) the liposomes encapsulating the gas can be conjugated with antibodies or other targeting moieties for the purpose of targeted delivery; and 4) the liposomes have acoustic reflectivity and thus can be located by ultrasound in vivo.

During the development of embodiments the present invention liposomes of phospholipid and cholesterol, were prepared by conventional procedures of hydrating the lipid film, sonication, freezing and thawing. A single, but important modification of this procedure generates liposomes that contain gas: after sonication, the lipid dispersion contains air in the amounts of about 10% by volume. The amount of encapsulation increases with gas pressure and lipid concentration. For example, in 0.32 M mannitol as the aqueous phase, 1, 2, 4, or 6 atm pressure applies to 4 mg of lipid leads to encapsulation of 10, 15, 20, and 27 ul gas, respectively. At 6 atm, doubling the concentration of lipids from 4 mg to 8 mg increased the amount of encapsulated gas from 27 ul to 55 ul. While mannitol solution generally gives the best encapsulation to date, it is not necessary as other reagents may be used. For example, in water, 20 ul gas can be encapsulated by 4 mg liposomes at 6 atm pressure. While the present invention is not limited to any mechanism, it is believed that this mechanism of gas encapsulation uses the fact that air (predominantly nitrogen and oxygen), like most solutes, dissolves poorly in ice and is excluded from ice that forms during freezing. As the air and lipid become mutually concentrated in the ever-diminishing liquid volume, air diffuses into the lipid. Then, either during freezing or upon thawing, the components of air come out of solution as pockets encapsulated within the lipid bilayers of the liposomes.

In the NO containing liposomes of embodiments of the present invention, the releasable NO amount can be adjusted by encapsulating NO and noble gas mixture in different ratios. This offers the ability to create a wide variety of NO releasing concentrations with variable clinical use. This type of control allows, for example, fundamental studies to be carried out that can define useful NO fluxes required to achieve specific therapeutic effects (e.g., inhibition of platelet activation, inhibition of bacterial growth, etc.). Additionally, the use of light as an on/off trigger to initiate release allows a means of temporal control of the NO flux. Such control would be important in efforts to potentially utilize local NO release within tumor masses to kill cancerous cells. This could be accomplished by coating the liposome material described here on the end of a fiber optic probe, inserting the probe precisely within the tumor mass, and delivering a defined NO dose by controlling the duration, intensity, and wavelength of light used to illuminate the fiber.

The vascular endothelium is a crucial regulator of vascular function and homeostasis. In addition to regulation of vascular tone and blood pressure, the vascular endothelium also has antithrombotic properties, modulates interactions between the blood vessel wall and circulating leukocytes and platelets, and acts as a paracrine organ by secretion of vasoactive substances that mitigate these varied functions. Nitric oxide (NO), previously known as endothelium-derived relaxing factor, is perhaps the most critical of the substances produced by the vascular endothelium for regulation of vasomotor tone. Nitric oxide (NO) is a molecule that dynamically modulates the physiological functions of the cardiovascular system, which include relaxation of vascular smooth muscle, inhibition of platelet aggregation, and regulation of immune responses. Because a reduced NO level has been implicated in the onset and progression of various disease states, NO may be used (via delivery by the liposomes described herein) to provide therapeutic benefits in the treatment of cardiovascular diseases, such as essential hypertension, stroke, coronary artery disease, atherosclerosis, platelet aggregation after percutaneous transluminal coronary angioplasty, and ischemia/reperfusion injury.

EXAMPLES

Example 1

Methods of Making and Testing Gas Containing Liposomes

This example described methods of making and testing gas containing liposome. The procedure involves a novel sequence of steps wherein the lipid suspension is equilibrated with the gas of choice under elevated pressure, frozen, returned to ambient pressure and thawed. This procedure allows large volumes of gas to be encapsulated in the liposomes.

Materials and Methods 1,2-dipalmitoyl-sn-glycero-3-phosphocholine (DPPC), 1,2-dioleoyl-sn-glycero-3-phosphocholine (DOPC), cholesterol (CH) and all other lipids were obtained from Avanti Polar Lipids (Alabaster, Ala.) and stored at −20° C. in chloroform. Argon was obtained from Airgas Inc.(Chicago, Ill.) and octafluorocyclobutane was from specialty gases of America, Inc. (Toledo Ohio). Calcein (2',7'-[(bis[carboxymethyl]-amino)methyl]-fluorescein) and cobalt chloride ($CoCl_2$) were obtained from Sigma Chemical Co.(St. Louis, Mo.). Stock solutions of calcein (80 mM) were made by rapidly dissolving solid calcein at pH 9.0 and then adjusting the pH to 7.5 with NaOH. Triton X-100 and 3-morpholinepropanesulphonic acid (MOPS) were also from Sigma. The sonoporation unit was a Sonitron1000, from RichMar (Inola, Okla.). Costar transwell insert with a 0.4 µm pore polyester membrane was from Corning Incorporated Life Sciences (Lowell, Mass.).

Gas-containing Liposome Preparation

Lipid mixtures (5 mg total weight) of the desired composition were prepared from chloroform solutions by combining the appropriate molar amounts of the component lipids in a 4 ml (15×45 mm) borosilicate glass test tube. The organic solvent was removed by evaporation under argon in a 50° C. water bath with constant rotation until a thin film of lipids was formed on the vial wall. The resulting lipid film was then placed under high vacuum (<100 mtorr) for 4-6 hours for complete removal of solvent. The dried lipid film was hydrated with 0.32M mannitol (mannitol is used in part as an osmoticant to provide physiologic osmolarity, but it also has beneficial effects for incorporation of air and entrapment of water soluble agents such as pharmaceutics) or other solutions of choice. The resultant liposomes (10 mg/ml final concentration) were sonicated for 5 min in a water bath. A total of 500 µl of the liposomal dispersion was transferred to 1.8 ml screw-cap borosilicate glass vials (12×32 mm) that were then capped with open screw caps containing Teflon-covered silicon rubber septa. The desired gas was introduced into the vial through the septum with a 10 ml syringe fitted with a 27 G×½" needle. The pressure created by the injected gas volume was calculated from Boyle's Law and the volumes of the vial and syringe. The septa used were tested for leakage at the highest pressure required in our investigation and found not to release detectable amounts of any of the three gases investigated for at least 24 hours. The pressurized-gas/liposome dispersion was incubated for ½ hour at room temperature and then frozen at −78° C. in dry ice for at least ½ hour. The pressure was released by unscrewing the caps immediately after their removal from dry ice. The depressured frozen liposomes were then thawed at room temperature. Gas encapsulation was measured after the sample had thawed and warmed to room temperature.

Liposome Preparation for Co-encapsulation of Gas and Calcein

Calcein, a fluorescent dye used as a marker of the liposome internal volume, was encapsulated by a procedure similar to that for preparing making gas-containing liposomes. To load the liposomes with calcein, 0.1 mM calcein was included in the 0.32 M mannitol normally used to hydrate the dried lipid film.

Measurement of the Amount of Gas into Lipid Dispersions

The amount of incorporated gas was determined using a previously described method (Huang et al., Ultrasound Med Biol 2002;28(3):339-48). Briefly, a 0.8-1 ml sample containing 5 mg lipid/ml is put into a 10-mL disposable syringe. A two-way Luerlock stopcock is attached to the syringe and the air is displaced from the syringe and stopcock by depressing the plunger. The stopcock is closed, and a 250-μL syringe, without a plunger, but containing a 20 ul volume of water is attached. The plunger of the large syringe is withdrawn to create a vacuum that releases air from the liposomes. After turning the stopcock to connect the large and small syringe bodies, and holding the large syringe so that the liposomes are at the bottom (away from the stopcock). The plunger is depressed to transfer the released air into the small syringe where its volume at ambient pressure is measured according to the displacement of the 20 ul bolus of water.

Determination of Calcein Encapsulation Efficiency

Aqueous phase encapsulation efficiency was determined fluorometrically using a previously developed method (Shohet, Circulation 2000;101(22):2554-6.). In the embodiment used here, a 25 μl aliquot of resuspended liposomes (10 mg lipid/ml) was diluted to 500 μl with 50 mM MOPS buffer containing 110 mM NaCl. Then, 5 μl of 10 mM $CoCl_2$ was added to quench the fluorescence of the external calcein so that the residual fluorescence represents the entrapped calcein. Then the liposomes were lysed with detergent (25 μl 10% Triton X-100) to determine the background fluorescence at zero encapsulated volume. Fluorescence intensity was measured before ($F_b$) and after ($F_a$) addition of $CoCl_2$, and again after addition of X-100 ($F_{totq}$) at 490 nm Ex, 520 nm Em. The % entrapment was calculated as:

$$\% \text{ encapsulation} = (F_a - F_{totq})/(F_b - F_{totq}) \times 100 \quad (1).$$

Ultrasound Imaging

To demonstrate ultrasound image enhancement (echogenicity), gas-containing liposomes, with or without encapsulated calcein, were diluted to a concentration of 25 μg/mL and placed in 12×16 mm glass vials. They were then imaged with a 20-MHz high-frequency intravascular ultrasound image catheter. Images were recorded onto videotape, subsequently digitalized and computer analyzed in terms of a 0-256 mean gray scale value (MGSV) of the entire image.

Ultrasound Triggered Release

Ultrasound-triggered release experiments were performed in a testing chamber. This chamber was composed of a Costar transwell insert with a 0.4 μm pore polyester membrane resting on a sheet of Rho-C rubber. A thin layer of water was placed between the membrane and the rubber to exclude air and air bubbles. The open top of the transwell insert allowed for introduction of the liposome dispersion (400 μl) and placement of the ultrasound probe.

The release of calcein was determined using a modified version of the encapsulation measurement procedure. 100 μl of calcein-containing, acoustically-active liposomes (10 mg lipid/mL), were diluted to 500 μl with 50 mM MOPS buffer containing 110 mM NaCl (to maintain isosmolality with liposome contents of 320 mM mannitol and 0.1 mM calcein). The fluorescence intensity ($F_{in}$) of the suspension was measured after addition of 5 μl of 40 mM $CoCl_2$. Ultrasound was then applied for 10 s and the resulting fluorescent intensity ($F_{ultrasound}$) was measured. Finally, 25 μl of 10% Triton X-100 was added and the fluorescent intensity ($F_{totq}$) was remeasured. Calcein release was calculated as:

$$[F_{in} - F_{ultrasound}]/[F_{in} - F_{totq}] \times 100 = \% \text{ release} \quad (2).$$

Statistical Analysis

Data are presented as mean±SD. Comparisons between groups were made by ANOVA with significance taken to be $P<0.05$.

Results

Preparation of Gas-containing Liposomes

As shown in FIG. 1, freezing the liposomal dispersion in the presence of elevated gas pressure led to gas entrapment in an amount that was related (essentially linearly over the range of pressures examined), to the pressure of the gas. With 0.32 M mannitol as the aqueous phase, 1, 2, 4 or 6 atm pressure applied to 4 mg of lipid led to incorporation of 10, 15, 20, and 30 μl air, respectively, into the dispersion. Given the dependence of air incorporation on the pressure, it appears that higher pressures would lead to even larger volumes of gas being incorporated into the lipid dispersion.

Figure 2:
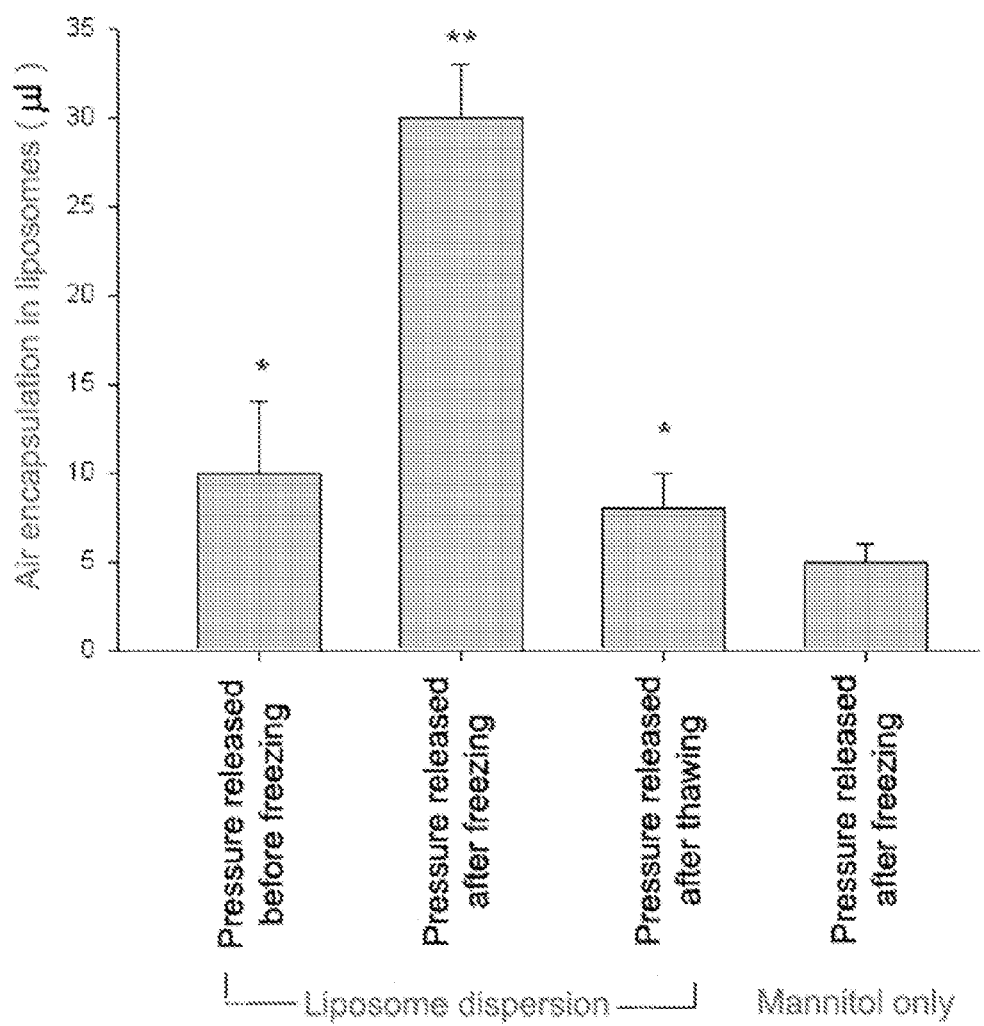
FIG. 2 shows the results from Example 1 where gas encapsulation was tested as a function of when pressure was released.

Freezing the dispersion is an important step in this procedure because a pressured liposomal dispersion without freezing did not incorporate adequate amounts of air to provide ultrasound contrast enhancement. It was therefore sought to be determined whether the pressure effect occurred before freezing, during freezing, or during thawing. For this test, liposomes were made by a procedure analogous to that described for gas-containing liposomes except that the pressure was released either before freezing or after thawing. As shown in FIG. 2, only a small amount of gas (10 μl) was taken up by the liposomal suspension when the pressure was released before the freezing step or after thawing step. The osmoticant mannitol solution without liposomes took up about 5-10 μl of gas. In contrast, when the pressure was released after freezing and before thawing, a much higher gas incorporation was measured (30 μl/4 mg lipid). These results indicate that the air is entrapped when the liposomes are frozen under applied pressure and thawed without pressure.

Effect of Solutes other than Mannitol on Gas Entrapment

Figure 3A:
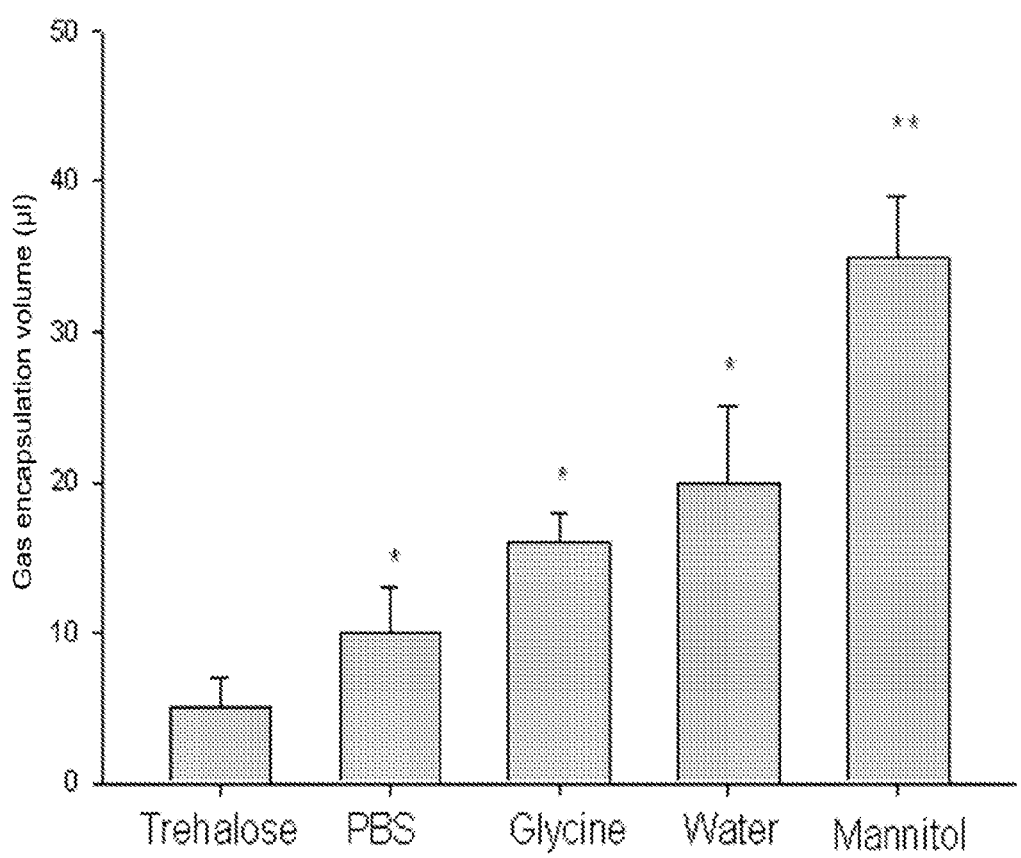
FIG. 3A shows the results from Example 1 where gas encapsulation was tested using different lipid film hydrating agents.

Mannitol was used in the hydrating phase because it had been found to be the best osmoticant (provides physiological osmolarity) for preparing echogenic liposomal dispersions by the previously described lyophilization-based procedure. As shown in FIG. 3a, mannitol provided the best gas encapsulation, about 30 μl gas in 5 mg liposomes. However, other solutions can also be used with reasonably good effect; in water, 20 μl of air was captured by 5 mg liposomes under 6 atm pressure. Non-cyroprotectant solutions like glycine and phosphate buffer (pH 7.4) also supported high air uptake. In the present of trehalose, air incorporation was low.

Encapsulation of an Aqueous Phase Marker; Encapsulation of Pharmaceutical Agents within Air-containing Liposomes As the air became incorporated after hydration of the lipid, we hypothesized that the air could be entrapped between the two constitutent monolayers of the lipid bilayers. Such a structure should allow co-encapsulation of drugs and gases in the same liposomes. Of particular interest were water-soluble drugs whose retention would be dependent upon the integrity of the vesicle, which, in turn, might be compromised by the pressure variation of an ultrasound wave. It was sought to be determined whether molecules in the aqueous phase could be encapsulated simultaneously with air or other gases. Liposomes were made by a procedure analogous to that described for gas-containing liposomes except that calcein, a fluorescent dye that is a convenient marker for encapsulation of the aqueous phase, was included (at 0.1 mM) in the mannitol solution and added in the lipid hydration step.

Figure 3B:
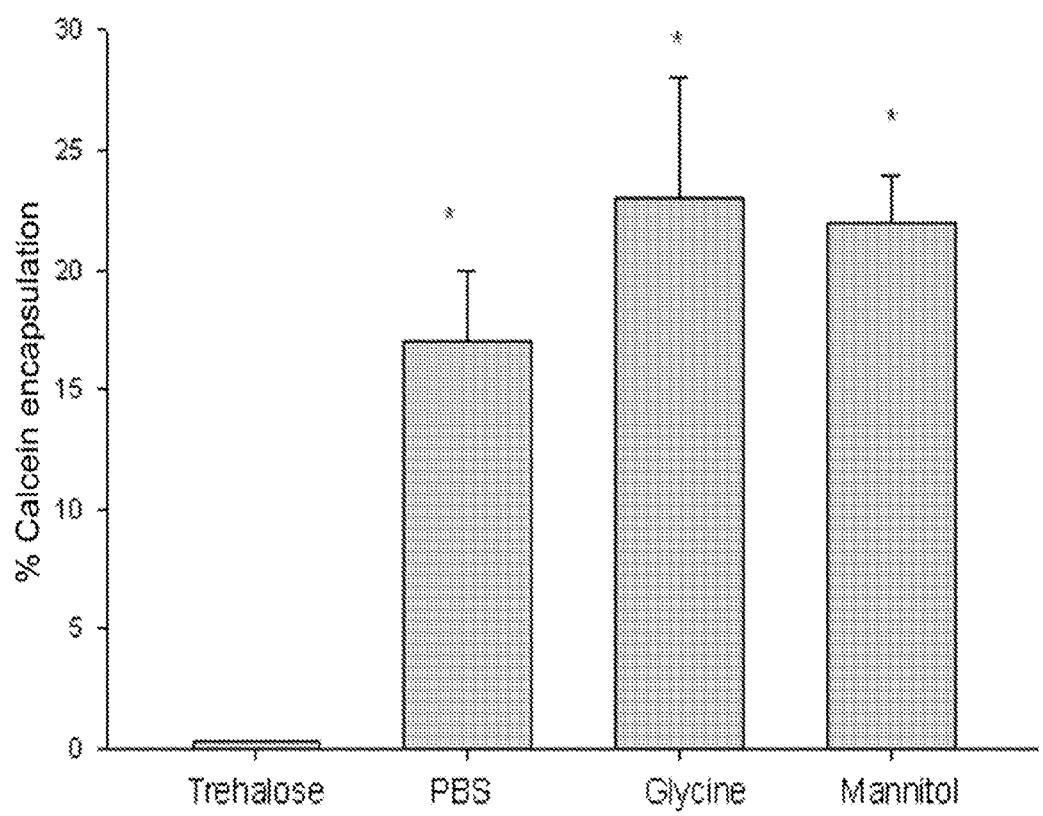
FIG. 3B shows the results from Example 1 where percentage of calcein encapsulation was tested as a function of different lipid film hydrating agents.

These aqueous marker encapsulation experiments demonstrated that this method leads to the production of true liposomes, i.e., particles characterized by an aqueous compartment separated from the bulk phase by a low-permeability membrane. As shown in FIG. 3b, three different osmoticants supported good calein encapsulation. Mannitol, glycine and PBS solutions gave 17%, 23% and 22% calcein encapsulation efficiency, respectively. Trehalose was again unsatisfactory as an osmoticant, giving very low calcein encapsulation.

Figure 4:
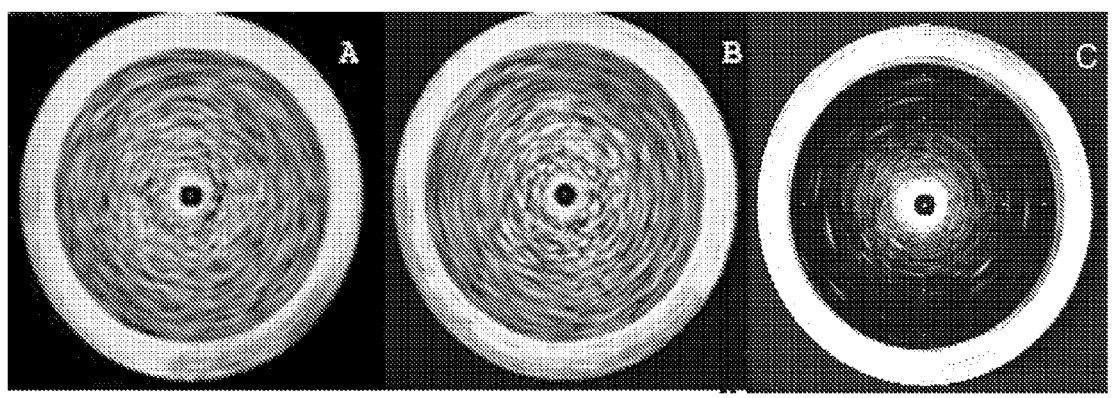
FIG. 4 shows echogenicity of liposomes without (A) or with (B) calcein encapsulation. and nongas-containing liposomes (C). Liposome composition: DPPC:DOPC:CH 35:35: 30. Mean +/− SD, Liposomes were imaged by 20 MHz intravascular catheter. (A) liposomes prepared with air pressure at 9 atm in the absence of calcein. The MGSV for this image is 124+/−10. (B) liposomes prepared so as to encapsulate both gas and calcein. The MGSV for this image is 118+/−12. (C) liposomes prepared by degassing under vacuum. The MGSV for this image is 12+/−3. Calcein uptake reveals that the gas-containing liposomes, like conventional liposomes, are capable of encapsulating a portion of the aqueous phase, including, of course, solutes (which could be drugs) contained therein.

As can be seen in FIG. 4, adequate echogenicity for good imaging was obtained with both gas encapsulation alone and with gas and calcein co-encapsulation.

Ultrasound Triggered Release of Aqueous Contents from Liposomes Containing Various Gases.

Figure 5:
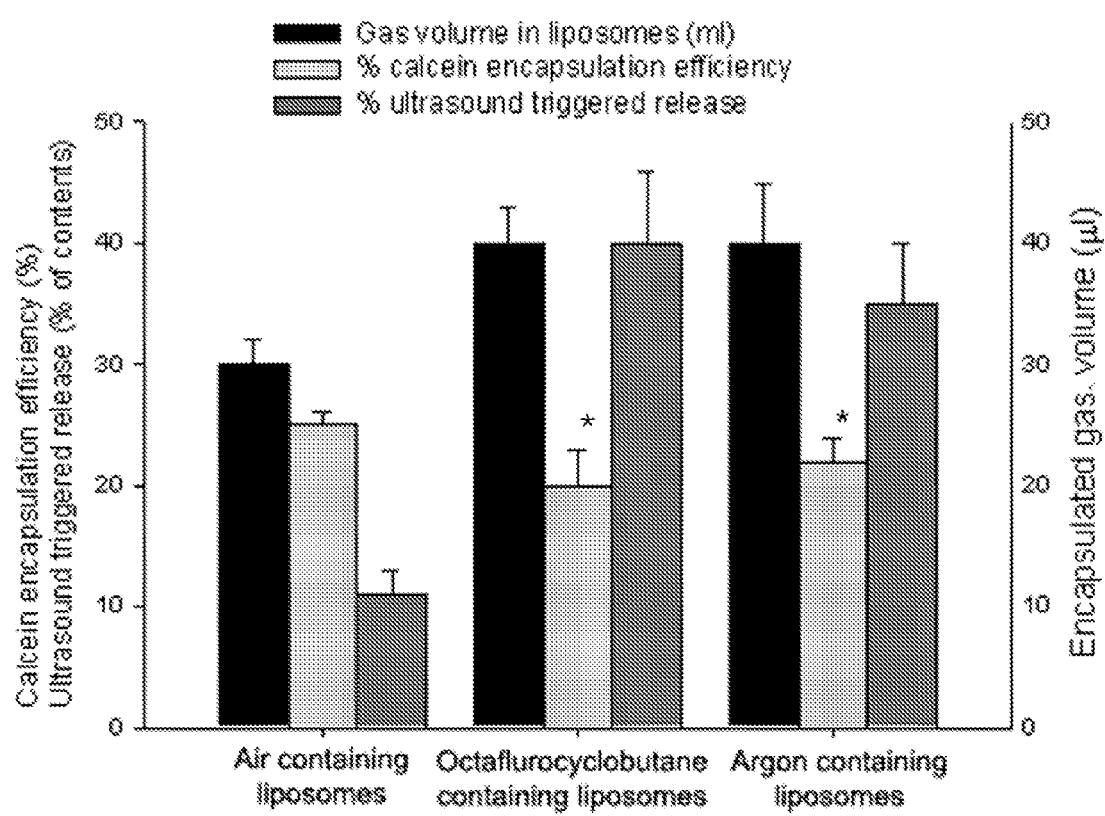
FIG. 5 shows results from Example 1 indicating that ultrasound assisted release could be used for liposomes containing three different types of gas (air, perfluorocyclobutane, and argon).

The potential for ultrasound-assisted release was tested using an 8 W/cm$^2$ therapeutic probe to insonate liposome samples encapsulating calcein and containing one of three different gases, air, perfluorocyclobutane, and argon. Ultrasound caused release of contents from all three types of liposomes, but, as shown in FIG. 5, the liposomes containing air were the least sensitive. Although encapsulation of calcein was very similar for all three sets of liposomes, the amount of gas incorporated was larger in the case of the cycloperfluorobutane- and argon-containing samples than for the air-containing samples. Ultrasound effected more release of contents from the latter samples than from the air-containing sample. As argon is much less expensive than the fluorocarbon but gave similar results, subsequent experiments were done on argon-containing preparations.

Figure 6:
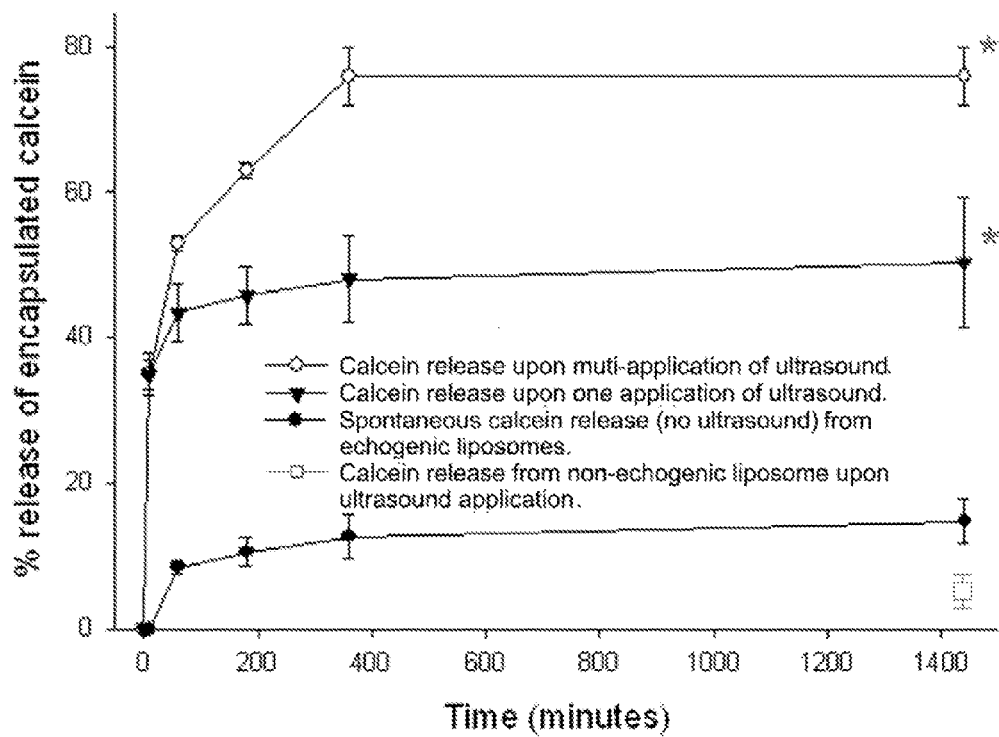
FIG. 6 shows the results from Example 1 where the amount of calcein release from liposomes was tested as a function of the type of, or lack of, ultrasound treatment.

Since conventional liposomes are susceptible to ultrasound damage, it was important to determine how much extra susceptibility to lysis was conferred by the presence of a gas. A comparison of argon-containing liposomes and non-echogenic liposomes (prepared without pressurization) with respect to ultrasound-assisted contents release between is shown in FIG. 6. The first application of ultrasound triggered the release of 23% of the entrapped calcein. Subsequent applications caused additional release and the combined effect of six applications was the release of a total of 42% of the initial contents.

Example 2

Methods of Making and Testing NO-Liposomes

This examples describes methods used to make NO-Liposomes and methods to test the rate of NO release from these liposomes. This example also describes methods used to test the use of NO ELIPs in an animal model for intimal hyperplasia.

Materials and Methods

Materials 1,2-Diopalmitoyl-sn-glycero-o-ethyl-3-phosphocholinel (EDPPC) was purchased from Genezyme Pharmaceuticals). 1,2-di-oleoyl-sn-glycero-3-phosphocholine (DOPC) and cholesterol (CH) were purchased from Avanti (Alabaster, Ala. ) and stored at −20 deg C. in chloroform.

Preparation of Nitric Oxide Loaded Liposomes

Liposomes were composed of EDPPC:DOPC:CH at a mole ratio of 60:30:10 in a glass vial. Lipids (5 mg total weight) were mixed in chloroform. The solvent was removed by evaporation under argon in a 50° C. water bath with constant rotation until a thin film of lipids was formed on the vial wall. The resulting lipid film was then placed under high vacuum (<100 Torr) for 4-6 hours for complete removal of solvent. The dried lipid film was hydrated with 0.32 M deoxygenated mannitol (15 min N$_2$ bubble). The resultant liposomes (10 mg/ml final concentration) were sonicated for 5 min in a water bath. The sonicated liposomes were transferred to a 2 ml volume glass vial with open top cap and sealed with Teflon rubber septa. Deoxygenated 5 M NaOH Nitric oxide or nitric oxide with argon mixture (1:1) in 10 ml volume was injected into vial through Teflon rubber septa by a 10 ml syringe with 27 G×½ needle. No leakage was found in such setting. Gas contained liposome dispersion was immediately frozen at a −70° C. dry ice for at least half hour. Frozen liposomes were then taken out. Caps were removed immediately to release pressure before any thawing. Gas encapsulation was measured after thawing.

NO Release Measured by Nitrite Accumulation

Figure 8:
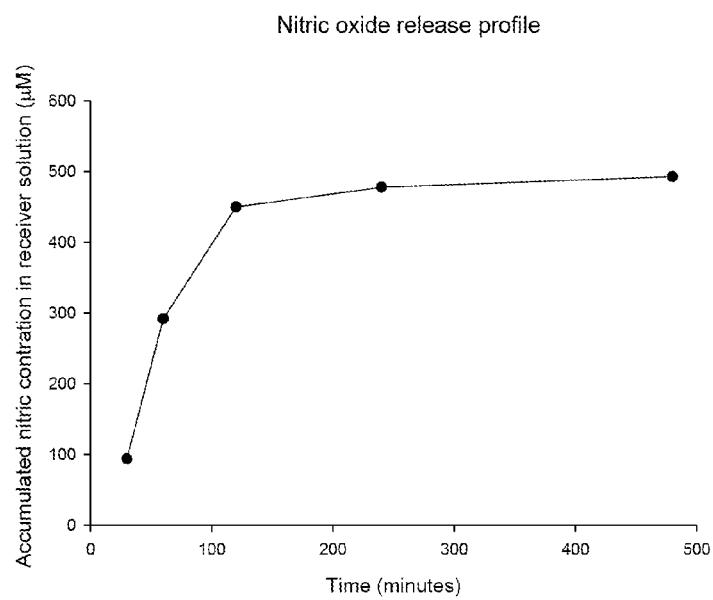
FIG. 8A shows results from Example 2 where nitric oxide released from NO containing liposomes into receiving solution was measured.
FIG. 8B shows nitric oxide release over time as determined in Example 2.
Figure 8:
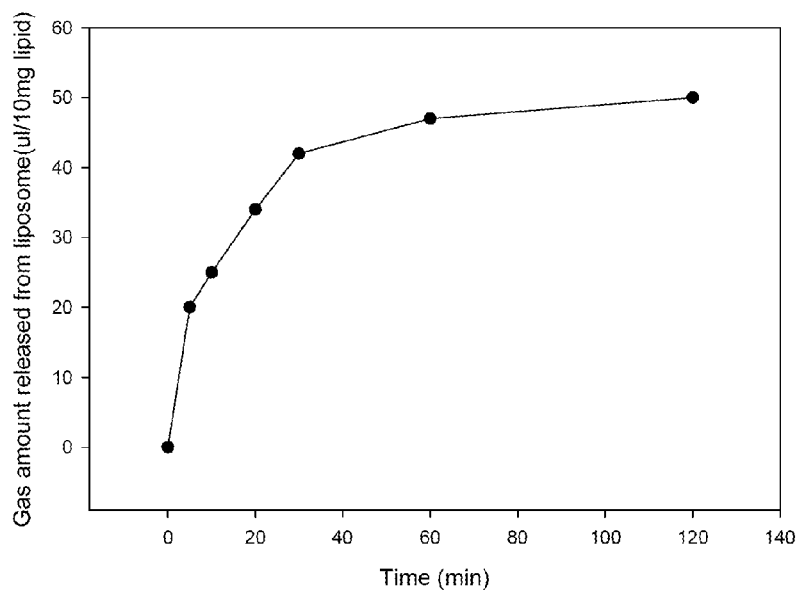

NO release from the nitric oxide loaded liposomes was measured by a dynamic dialysis technique monitoring the nitric oxide concentration in the receiver solution. According to the method, the nitric oxide is first released from the liposomes into the donor solution contained in the dialysis bag. Because of the short half-life of NO in aqueous solution and its reaction with oxygen in water to yield nitrite ($4NO+O_2+2H_2O \rightarrow 4NO_2^- +4H^+$)$^2$, the formed nitric can diffuse through the dialysis bag in the receiver solution where the nitric concentration was determined for extended periods of time. The dialysis bag containing 180 µl phosphate-buffered saline (PBS) was inserted into an cell contains 1 ml receiver buffer (PBS). 20 µl of sample was added into the bag. At different time intervals of 0, 5 min, 10 min, 20 min, 30 min, 60 min, 120 min, 240 min and 480 min, the samples were transferred to a fresh cell of receiver solution, and the nitrite accumulation was measured in each receiver solution following the sample transfer by a fluorometric nitric oxide assay kit according to company provided method (Calbiochem, USA). Nitric diffusion can be affected by the existence of nitrite in the outside of liposomes. A nitric oxide loaded mannitol solution, prepared in the same way with nitric oxide loaded lipsomes except in the absence of liposomes, was used as a control. The nitrite concentration in the sample receiver solution subtracted by the nitrite concentration in the control receiver solution was taken to be equivalent to the NO released from the liposomes during each time period. The results are shown in FIG. 8A.

Direct Measurement of Gas Contained in Liposomes

Figure 7:
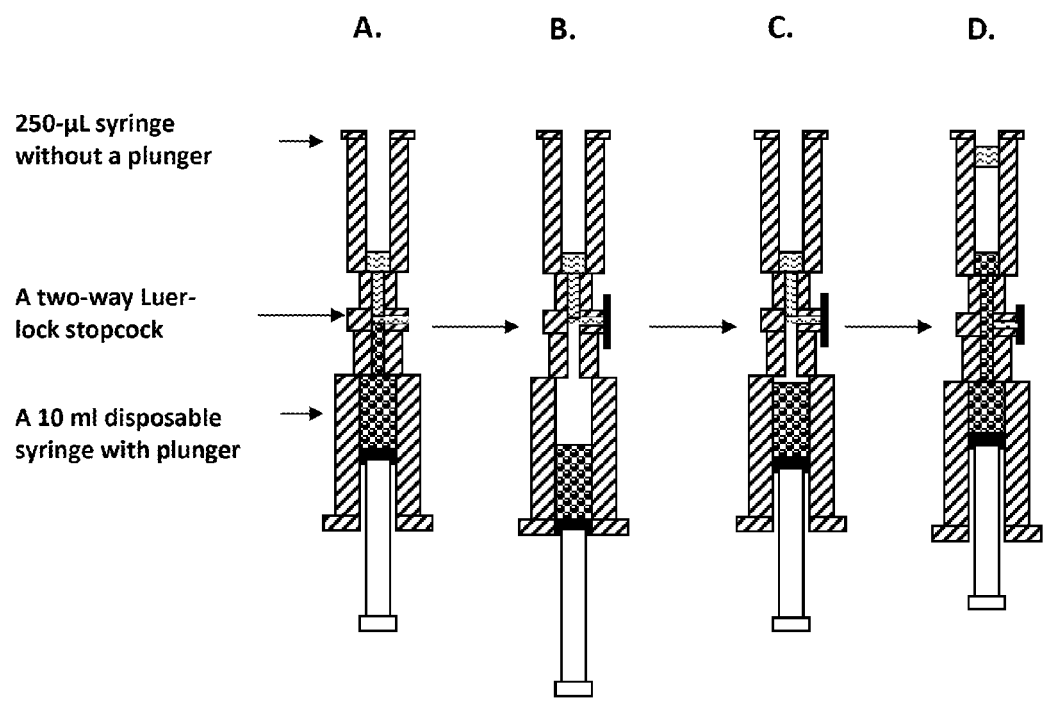
FIG. 7 shows the device used in the syringe method used to measure gas contained in liposomes in Example 2.

The gas contained in liposomes was measured with a syringe method. The sample, typically, 2 to 3 mL and 10 mg/mL, was contained in a 10-mL disposable syringe attached to the syringe and air was displaced from the syringe and stopcock by depressing the plunger. The stopcock was closed, and a 250-µL syringe without a plunger, but containing a small volume of water (e.g., 30 µL) (FIG. 7A), was connected to the other side of the stopcock. The plunger of the large syringe was then withdrawn, typically to 2 or 3 times the volume of the dispersion, generating a vacuum of approximately 0.03 to 0.06 atm (FIG. 7B). It is noted that the lower pressure limit is due to vapor pressure of water and the upper limit is that which would result from the largest release of air that has been observed. The vacuum was held for the desired length of time, and when the plunger was released, it returned to a position corresponding to a volume slightly larger than the original, due to the air released from the dispersion (FIG. 7C). This air pocket, which rose to the top of the dispersion, was displaced (upward) into the barrel of the microliter syringe by depressing the plunger of the large syringe after opening the stopcock (FIG. 7D). The volume of released air, now contained between two columns of liquid (water at the top and dispersion at the bottom) was then accurately read from the microliter syringe scale.

Cell Culture

Rat vascular smooth muscle cells (VSMC) (American Type Culture Collection, Bethesda, Md., USA) were grown in 75-cm$^2$ flask in DMEM (GIBCO-BRL, USA) containing 20% fetal bovine serum (FBS), 100 units/m penicillin and 100 mg/ml streptomycin at 37° C. under 5% $CO_2$ and 95% air. The cells used in this study were between passages 5-8. Cells grew to confluence in about 3 days. Cells were then passaged with 0.25% trypsin/1 mM EDTA (GIBCO-BRL, USA).

Nitric Oxide Uptake Measured by Fluorometric NO Image

To determine if the nitric oxide was delivered into cells by liposomes, a DAF-2/DA fluorometric NO detection system was used (see, Nakatsubo, et al., FEBS Lett 1998;427(2):263-6, herein incorporated by reference). The culture medium was changed to serum-free medium 24 hours before the experiment and the cells were further incubated at 37° C. After another 12 hours, the ECs were washed twice with PBS and PBS containing 1 µM DAF-4, 100 µM -arginine, 1 µM bradykinin, and an appropriate concentration of L-NAME or D-NAME was added. After further incubation for 30, 60, and 120 min, the supernatants were transferred to black microplates and the fluorescence was measured with a fluorescence microplate reader calibrated for excitation at 485 nm and emission at 538 nm.

Cell Variability

Figure 9:
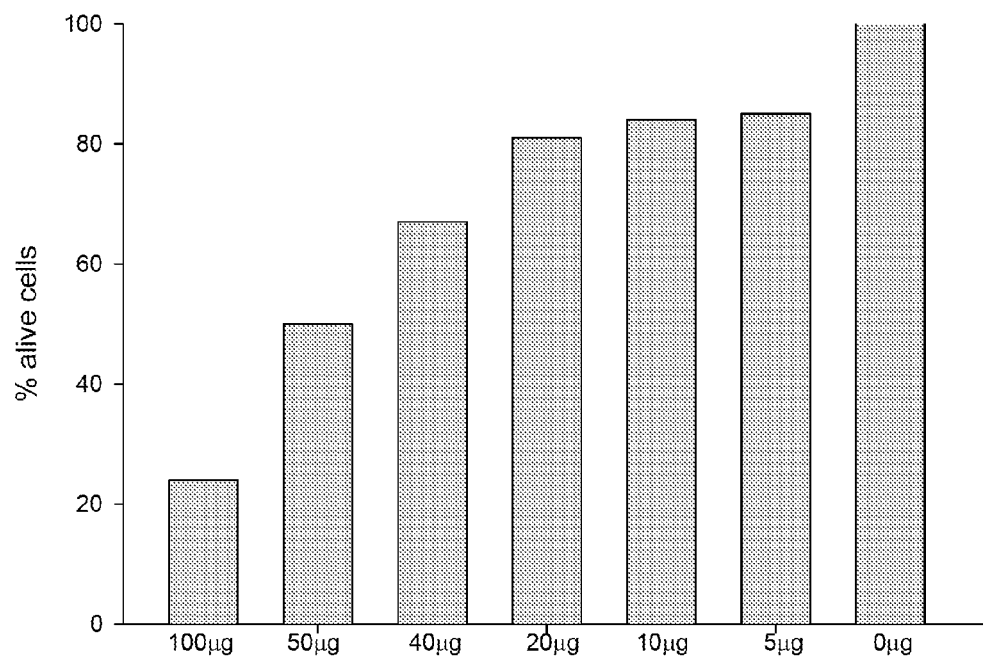
FIG. 9 shows cell viability at 4 hours after NO loaded liposome delivery as measured in Example 2.

VSMC cells were seeded in 48 wells at a density of 300,000 cells/cm$^2$ and grown for 20 hours in DMEM with 10% FCS. The medium was removed, replaced with DMEM 0.3 3% FCS at the desired NO-liposome concentration and the cells were incubated at 37° C. for 6 hours. After incubation, the medium was removed, the cells were washed twice with 2 ml PBS and variability was measured by commercial available calcein AM kit. The results are shown in FIG. 9.

Balloon Injury and Local Delivery of NO-Liposomes

All animal experiments were performed with the approval of the ethics committee for animal experimentation of the University of Texas Health Science Center. A total of 32 male New Zealand White rabbits weighing 3.0-4.5 kg were used in this study. The animals were fed with high cholesterol diet for two weeks before operation. In the day of operation, rabbits were anesthetized under general anesthesia with ketamine (35 mg/kg) and xylazine (5 mg/kg). Angioplasty of the common carotid artery was performed using a 2 F balloon catheter. The balloon catheter was introduced through the right external carotid artery into the common carotid artery. The balloon was then inflated with 200 ul saline and back and forth for 3 times in the middle segment (3 cm length) of the right injured carotid artery. At the time of balloon injury, NO liposomes were applied intravascularly.

Morphology

The rabbits were killed at 2 weeks after the injury. The animals were anesthetized, and the carotid artery were taken out and cut into 8-10 blocks and fixed with phosphate-buffered saline containing 4% formaldehyde for 24 hours. The fixed vascular were embedded in paraffin. Hematoxylineosin and elastica stains were used for morphological examinations. The cross-sectional areas of external elastic membrane (EEL), internal elastic membrane (IEL), lumen, media, and neointima were measured using a computerized image analysis system, and the ratios between neointima and media were calculated (8, 9, 12, 14).

To investigate the effect of balloon dilation on the arterial remodeling, the obtained external elastic lamina circumference measures (EELc) were normalized by the EELc measure of the controlateral noninjured carotid of the same animal; this parameter represented the remodeling normalized ratio (RNR).

Statistical Analysis

All data are shown as means±SE. Statistical analysis between groups was performed by two-way ANOVA with a SPSS version 8.0 program. A value of $P<0.05$ was considered significant.

Results

Nitric Oxide Encapsulation and Release

NO encapsulation and release from NO-liposomes was first investigated by gas volume measurement. As showed in FIG. 8B, a total of 50 µl of NO can be encapsulated in 5 mg of ELIP by the pressured frozen method. A spontaneous release of NO from ELIP has been seen. The release is fast in first half hour and slows down afterward. 50% of encapsulated gas was released within a half hour. The total amount of NO available to be released and the achieved NO concentration can be adjusted by mixing NO with argon.

Figure 10:
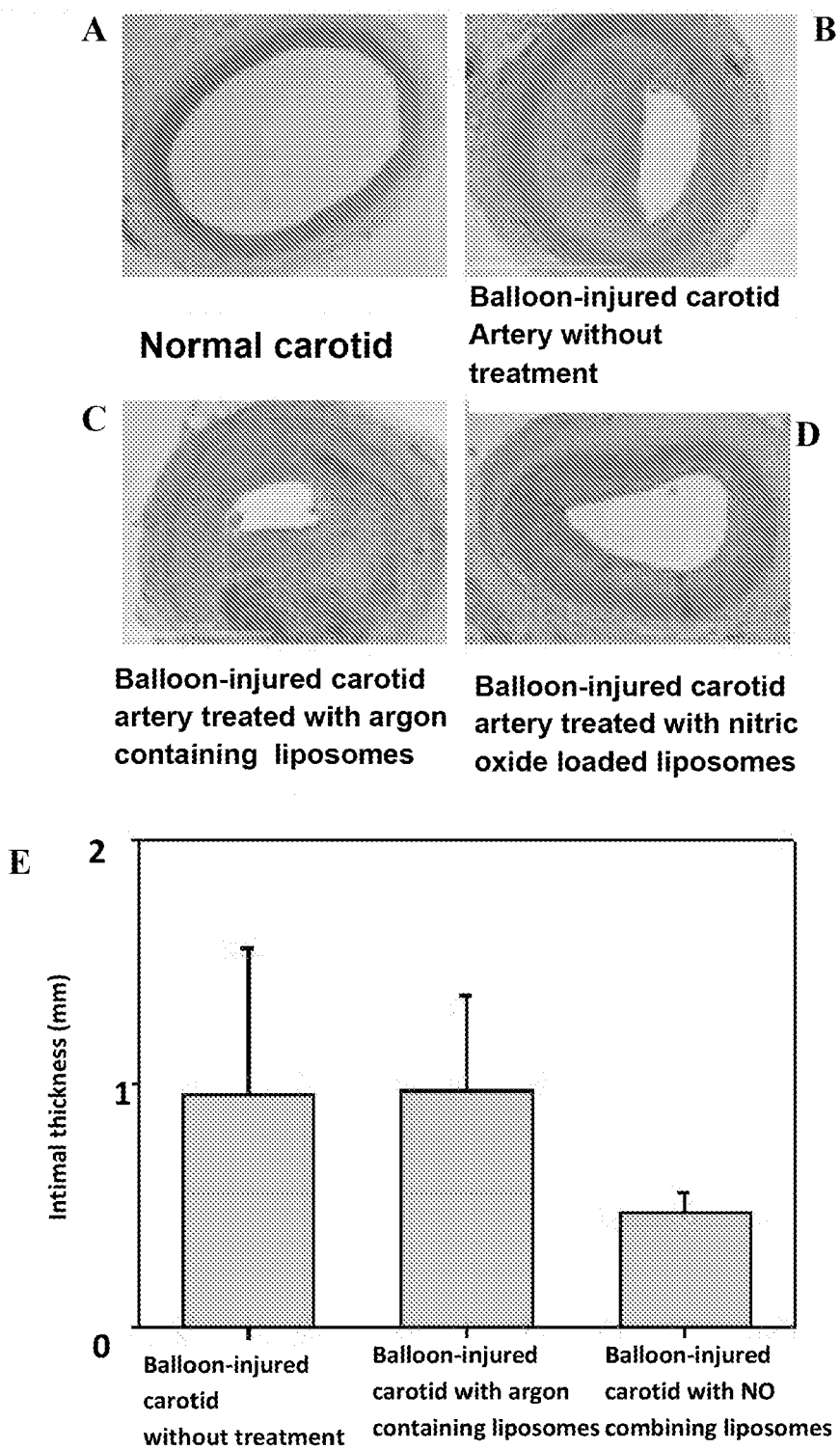
FIG. 10 shows, representative histological cross sections stained with hematoxylin-eosin. A: common carotid artery from a normal rat (no balloon injury); B: common carotid artery 14 days after injury using the angioplasty balloon catheter; C: argon containing liposome treated angioplastic common carotid artery 14 days after injury and treatment; D: NO containing liposome treated angioplastic common carotid artery 14 days after injury and treatment; and E: histogram demonstrating intimal thickness of carotid arteris under the conditions, of B-D.

In sham-operated rats that were not subjected to vascular injury, no neointimal formation was detected. FIG. 10 shows representative histological cross sections of carotid arteries after dilation with balloon catheter and treated with NO-liposomes compared with a normal carotid section and with no treatment or treated with argon-liposomes. It is worth noting that to standardize the arterial dimensions (that may vary depending on the animal body surface area), the EELc measures were normalized by the measure of the EELc of the controlateral noninjured carotid of the same animal and the variation in arterial dimension were expressed as RNR (FIG. 10b). A significant reduction of the RNR in NO-liposome treated group was observed.

Example 3

Multi-functional liposomes for Image-Guided and Ultrasound-controlled PPAR Agonist Delivery Introduction: The peroxisome proliferator activated receptor (PPAR) agonist rosiglitazone has been reported to yield cardiovascular benefits in atheroclothesis treatment. The efficient delivery of a PPAR agonist to its designated site of action is a challenging problem. The present invention contemplates that liposomes that co-encapsulate gas and drugs allow ultrasound image-guided delivery and ultrasound controlled release.

Methods: Cationic liposomes of phospholipid and cholesterol, were prepared by conventional procedures of hydrating the lipid film, sonication, freezing and thawing. A single, but important modification of this procedure generates liposomes that contain gas; after sonication, the lipid is put under pressure using air. After equilibration, the sample is frozen. When the pressure is reduced to atmospheric and the suspension thawed, rosiglitazone formed complexes with hydroxypropyl-beta-cyclodextrin complexes to improve its solubility. Complexes were then added to lipids in the hydration step. A 20 MHz Intravascular ultrasound image was performed after thawing liposomes. Ultrasound-triggered release was achieved by applying 1 MHz ultrasound at 2 W/cm2 for 10 s in a setting that ultrasound reflection was minimized. Such gas-rosiglitazone co-encapsulated liposomes were delivered to cultured vascular smooth muscle cells and its effect on the inhibition of proliferation was tested.

Results: When complexes formed with hydroxypropyl-beta-cyclodextrin, the solubility of rosiglitazone improved seven hundred times. That allows rosiglitazone to be encapsulated into the hydrophilic phase of liposomes. This method resulted a gas-rosiglitazone co-encapsulated liposomes with gas encapsulation efficiency of 30 μl per 5 mg liposomes and rosiglitazone encapsulation efficiency of 35%. Ultrasound triggered a 20% of contents release. Such liposomes can also be imaged by ultrasound. The drug encapsulation did not affect echogenicity. When delivered to cells, it resulted a 50% inhibition of proliferation.

Conclusion: This comprehensive drug delivery system will possess numerous advantages over existing treatment approaches, with the highlight being its use of medical imaging modalities for minimally invasive placement, characterization and therapeutic evaluation. In addition, its release of contents can be controlled. Such liposomes allow the development of a highly effective delivery system for site-specific treatment.

All publications and patents mentioned in the above specification are herein incorporated by reference. Various modifications and variations of the described compositions, methods, and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in art are intended to be within the scope of the following claims.

We claim:

1. A method of making a gas-containing liposome, comprising the following steps in the recited order:
   a) combining hydrated liposomes with gas under elevated pressure to generate a hydrated gas-liposome dispersion;
   b) freezing said hydrated gas-liposome dispersion to generate a frozen hydrated gas-liposome dispersion;
   c) reducing pressure on said frozen hydrated gas-liposome dispersion to atmospheric pressure; and
   d) thawing said frozen hydrated gas-liposome dispersion to generate a plurality of gas-containing liposomes, wherein a volume of said gas is encapsulated in each of said gas-containing liposomes, and wherein said plurality of gas-containing liposomes contain at least 20 μl of gas per 5 mg of said plurality of gas-containing liposomes.

2. The method of claim 1, wherein said plurality of gas-containing liposomes comprise at least 30 ul of gas per 5 mg of said gas-containing liposomes.

3. The method of claim 1, wherein said gas is selected from air, nitric oxide, a perflourocarbon, argon, and carbon monoxide.

4. The method of claim 1, further comprising co-encapsulating aqueous solutes with said gas in said gas-containing liposomes.

5. The method of claim 4, wherein said aqueous solutes comprise a therapeutic agent useful in the treatment of atherosclerosis.

6. The method of claim 5, wherein said therapeutic agent comprises rosiglitazone.

7. The method of claim 1, wherein said gas-containing liposomes each comprise nitric oxide and a second gas, wherein said second gas is configured to regulate the release rate of said nitric oxide from said liposome.

* * * * *